United States Patent
Sakuma et al.

(10) Patent No.: US 10,793,603 B2
(45) Date of Patent: Oct. 6, 2020

(54) POLYSACCHARIDE DERIVATIVE HAVING MEMBRANE-PERMEABLE PEPTIDE CHAIN

(71) Applicants: JOSHO GAKUEN EDUCATIONAL FOUNDATION, Osaka (JP); ADEKA CORPORATION, Tokyo (JP)

(72) Inventors: Shinji Sakuma, Osaka (JP); Kohta Mohri, Osaka (JP); Ken-ichiro Hiwatari, Tokyo (JP); Kyohei Ochiai, Tokyo (JP)

(73) Assignees: JOSHO GAKUEN EDUCATIONAL FOUNDATION, Osaka (JP); ADEKA CORPORATION, Tokyo (JP)

( * ) Notice: Subject to any disclaimer, the term of this patent is extended or adjusted under 35 U.S.C. 154(b) by 48 days.

(21) Appl. No.: 15/547,595

(22) PCT Filed: Feb. 23, 2016

(86) PCT No.: PCT/JP2016/055173
§ 371 (c)(1),
(2) Date: Jul. 31, 2017

(87) PCT Pub. No.: WO2016/136707
PCT Pub. Date: Sep. 1, 2016

(65) Prior Publication Data
US 2018/0044381 A1    Feb. 15, 2018

(30) Foreign Application Priority Data
Feb. 27, 2015  (JP) .................. 2015-038432

(51) Int. Cl.
| | |
|---|---|
| *C07K 9/00* | (2006.01) |
| *C08B 37/08* | (2006.01) |
| *C08B 37/00* | (2006.01) |
| *A61K 47/36* | (2006.01) |
| *A61K 47/42* | (2017.01) |
| *A61K 47/30* | (2006.01) |
| *C08L 5/08* | (2006.01) |
| *A61K 38/14* | (2006.01) |
| *C07K 17/10* | (2006.01) |

(52) U.S. Cl.
CPC .............. *C07K 9/001* (2013.01); *A61K 38/14* (2013.01); *A61K 47/30* (2013.01); *A61K 47/36* (2013.01); *A61K 47/42* (2013.01); *C07K 9/00* (2013.01); *C07K 17/10* (2013.01); *C08B 37/0045* (2013.01); *C08B 37/0072* (2013.01); *C08L 5/08* (2013.01)

(58) Field of Classification Search
CPC combination set(s) only.
See application file for complete search history.

(56) References Cited

U.S. PATENT DOCUMENTS

| | | | |
|---|---|---|---|
| 5,548,062 A | 8/1996 | Isoai et al. | |
| 2003/0229202 A1 | 12/2003 | Guo et al. | |
| 2004/0167098 A1 | 8/2004 | Barbucci et al. | |
| 2010/0061932 A1* | 3/2010 | Brock | C07K 14/79 424/9.1 |
| 2010/0113559 A1 | 5/2010 | Park et al. | |
| 2012/0010124 A9* | 1/2012 | Alluis | A61K 31/74 514/1.3 |
| 2013/0338352 A1 | 12/2013 | Yasugi et al. | |

(Continued)

FOREIGN PATENT DOCUMENTS

| | | |
|---|---|---|
| CN | 104245722 | 12/2014 |
| EP | 0 671 412 | 9/1995 |

(Continued)

OTHER PUBLICATIONS

Tang et al., "Tat-conjugated hyaluronic acid enveloping polyplexes with facilitated nuclear entry and improved transfection" Colloids and Surfaces A: Physiochemical and Engineering Aspects vol. 423 pp. 124-130 (Year: 2013).*

(Continued)

*Primary Examiner* — Eric Olson
(74) *Attorney, Agent, or Firm* — Nixon & Vanderhye

(57) ABSTRACT

A polysaccharide derivative has a partial structure represented by Formula (1) below. It is preferable that at least one of the amino acids that constitute $X^2$ in Formula (1) below is a basic amino acid.

(1)

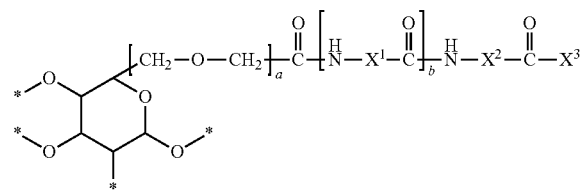

(In the formula, $X^1$ represents a residue obtained by removing the terminal amino group and the terminal carboxyl group from a neutral amino acid or an ω-aminoalkanoic acid, $X^2$ represents a residue obtained by removing the terminal amino group and the terminal carboxyl group from a membrane-permeable peptide, $X^3$ represents a hydroxyl group, an amino group, an alkoxyl group having 1 to 4 carbon atoms, or a benzyloxy group, a represents a number of 0 or 1, and b represents a number of from 0 to 50.)

11 Claims, No Drawings
Specification includes a Sequence Listing.

(56) References Cited

U.S. PATENT DOCUMENTS

| | | | | |
|---|---|---|---|---|
| 2014/0124929 A1* | 5/2014 | Lin | ......................... | H01L 24/05 257/738 |
| 2014/0140929 A1* | 5/2014 | Ahmed | .............. | A61K 49/0004 424/9.1 |
| 2015/0038678 A1 | 2/2015 | Eaton et al. | | |

FOREIGN PATENT DOCUMENTS

| | | |
|---|---|---|
| EP | 1 797 901 | 6/2007 |
| JP | 4-134096 | 5/1992 |
| JP | 4-300900 | 10/1992 |
| JP | 3162069 | 4/2001 |
| JP | 2004-261024 A | 9/2004 |
| JP | 2005-52083 | 3/2005 |
| JP | 2007-145761 A | 6/2007 |
| JP | 2010-100781 | 5/2010 |
| JP | 2010-515678 | 5/2010 |
| JP | 2011-229495 | 11/2011 |
| WO | WO 2012/118189 | 9/2012 |

OTHER PUBLICATIONS

Wang et al., "Mucosal immunization with a DNA vaccine induces immune responses against HIV-I at a mucosal site" Vaccine vol. 15 No. 8 pp. 821-825 (Year: 1997).*

Brooks et al., "Tat peptide-mediated cellular delivery: back to basics" Advanced Drug Delivery Reviews vol. 57 pp. 559-577 (Year: 2005).*

International Search Report dated May 24, 2016 in corresponding International Application No. PCT/JP2016/055173.

Extended European Search Report for Application No. 16755451, dated Oct. 22, 2018.

* cited by examiner

SEQUENCE LISTING

```
<160> NUMBER OF SEQ ID NOS: 12

<210> SEQ ID NO 1
<211> LENGTH: 13
<212> TYPE: PRT
<213> ORGANISM: Artificial Sequence
<220> FEATURE:
<223> OTHER INFORMATION: Hydrophilic basic peptide

<400> SEQUENCE: 1

Gly Arg Lys Lys Arg Arg Gln Arg Arg Arg Pro Pro Gln
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Hydrophilic basic peptide

<400> SEQUENCE: 2

Thr Arg Gln Ala Arg Arg Asn Arg Arg Arg Arg Trp Arg Glu Arg Gln
1               5                   10                  15

Arg

<210> SEQ ID NO 3
<211> LENGTH: 15
<212> TYPE: PRT
<213> ORGANISM: Artificial Sequence
<220> FEATURE:
<223> OTHER INFORMATION: Hydrophilic basic peptide

<400> SEQUENCE: 3

Arg Arg Arg Arg Asn Arg Thr Arg Arg Asn Arg Arg Arg Val Arg
1               5                   10                  15

<210> SEQ ID NO 4
<211> LENGTH: 13
<212> TYPE: PRT
<213> ORGANISM: Artificial Sequence
<220> FEATURE:
<223> OTHER INFORMATION: Hydrophilic basic peptide

<400> SEQUENCE: 4

Thr Arg Arg Gln Arg Thr Arg Arg Ala Arg Arg Asn Arg
1               5                   10

<210> SEQ ID NO 5
<211> LENGTH: 19
<212> TYPE: PRT
<213> ORGANISM: Artificial Sequence
<220> FEATURE:
```

```
<223> OTHER INFORMATION: Hydrophilic basic peptide

<400> SEQUENCE: 5

Lys Leu Thr Arg Ala Gln Arg Arg Ala Ala Ala Arg Lys Asn Lys Arg
1               5                   10                  15

Asn Thr Arg

<210> SEQ ID NO 6
<211> LENGTH: 16
<212> TYPE: PRT
<213> ORGANISM: Artificial Sequence
<220> FEATURE:
<223> OTHER INFORMATION: Amphiphilic basic peptide

<400> SEQUENCE: 6

Arg Gln Ile Lys Ile Trp Phe Gln Asn Arg Arg Met Lys Trp Lys Lys
1               5                   10                  15

<210> SEQ ID NO 7
<211> LENGTH: 19
<212> TYPE: PRT
<213> ORGANISM: Artificial Sequence
<220> FEATURE:
<223> OTHER INFORMATION: Amphiphilic basic peptide

<400> SEQUENCE: 7

Lys Met Thr Arg Ala Gln Arg Arg Ala Ala Ala Arg Arg Asn Arg Trp
1               5                   10                  15

Thr Ala Arg

<210> SEQ ID NO 8
<211> LENGTH: 16
<212> TYPE: PRT
<213> ORGANISM: Artificial Sequence
<220> FEATURE:
<223> OTHER INFORMATION: Amphiphilic basic peptide

<400> SEQUENCE: 8

Arg Gln Ile Lys Ile Trp Phe Gln Asn Arg Arg Met Lys Trp Lys Lys
1               5                   10                  15

<210> SEQ ID NO 9
<211> LENGTH: 17
<212> TYPE: PRT
<213> ORGANISM: Artificial Sequence
<220> FEATURE:
<223> OTHER INFORMATION: Amphiphilic basic peptide

<400> SEQUENCE: 9

Asn Ala Lys Thr Arg Arg His Glu Arg Arg Arg Lys Leu Ala Ile Glu
1               5                   10                  15

Arg

<210> SEQ ID NO 10
<211> LENGTH: 34
<212> TYPE: PRT
<213> ORGANISM: Artificial Sequence
<220> FEATURE:
<223> OTHER INFORMATION: Amphiphilic basic peptide

<400> SEQUENCE: 10

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Asp Asp Pro
```

```
Val Asp

<210> SEQ ID NO 11
<211> LENGTH: 27
<212> TYPE: PRT
<213> ORGANISM: Artificial Sequence
<220> FEATURE:
<223> OTHER INFORMATION: Hydrophobic basic peptide

<400> SEQUENCE: 11

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 12
<211> LENGTH: 21
<212> TYPE: PRT
<213> ORGANISM: Artificial Sequence
<220> FEATURE:
<223> OTHER INFORMATION: Hydrophobic basic peptide

<400> SEQUENCE: 12

Ala Gly Tyr Leu Leu Gly Lys Ile Asn Leu Lys Ala Leu Ala Ala Leu
1               5                   10                  15

Ala Lys Lys Ile Leu
            20
```

POLYSACCHARIDE DERIVATIVE HAVING MEMBRANE-PERMEABLE PEPTIDE CHAIN

TECHNICAL FIELD

The present invention relates to a polysaccharide derivative that is useful for introducing a poorly membrane-permeable compound into a cell or a mucous membrane.

BACKGROUND ART

In recent years, attempts have been made to elucidate functions of synthetic peptides, proteins, DNAs, and sugars or induce special functions by introducing these substances into a cell to adjust intracellular protein interaction and control intracellular signaling, transcription, or the like. With such an approach, it can be expected that genetic information that has been considered to be a mystery is elucidated, the causes of diseases are elucidated, and methods for treating the diseases are developed. Moreover, due to development of ES cells and iPS cells, a technique for controlling cell functions with nucleic acids or proteins becomes more important.

Water-soluble polymer substances such as polypeptides, nucleic acids, and sugars are usually highly hydrophilic, and thus have difficulty in passing through a cell membrane. Therefore, a microinjection method, an electroporation method, a calcium phosphate method, a lipofection method, a viral vector method, a membrane-permeable peptide method, and the like are known as a method for introducing these substances into a cell.

Of these methods, the membrane-permeable peptide method is a method that utilizes macropinocytosis of a cell induced by a membrane-permeable peptide. A method in which a target compound to be introduced into a cell and a membrane-permeable peptide are covalently bound and introduced (see Patent Literature 1 and 2, for example), and a method in which a polymer compound having a membrane-permeable peptide in a side chain and a target compound to be introduced into a cell are allowed to coexist and only the target compound is introduced (see Patent Literature 3 and 4, for example) are known as the membrane-permeable peptide method. With the method in which a target compound and a membrane-permeable peptide are covalently bound and introduced, cells are less damaged, but complex pretreatment is needed. On the other hand, the method using a polymer compound having a membrane-permeable peptide in a side chain is simple, but a conventionally known polymer compound having a membrane-permeable peptide in a side chain has a slightly high cytotoxicity, and a concentration at which the polymer compound is used is sometimes limited. Therefore, there is a problem with such a polymer compound when the efficiency of introducing the target compound is improved.

Also, the application of the polymer having a membrane-permeable peptide in a side chain to an agent for promoting the absorption of a medicine from the epithelium (see Patent Literature 5, for example) is proposed, but the polymer has a mucous membrane irritating property, which causes a problem when the agent is put into practical use.

On the other hand, it is known that a compound obtained by cross-linking polysaccharides having a carboxyl group using polyamine (see Patent Literature 6, for example) is useful as a thickener, a lubricant, a gelling agent, and the like in a medical field, a drug field, and a skin cosmetics field. However, a compound obtained through reaction between a polysaccharide having a carboxyl group and a membrane-permeable peptide is unknown.

CITATION LIST

Patent Literature

Patent Literature 1: US 2003/229202A1
Patent Literature 2: JP 2005-052083A
Patent Literature 3: US 2010/113559A1
Patent Literature 4: JP 2011-229495A
Patent Literature 5: JP 2010-100781A
Patent Literature 6: US 2004/167098A1

SUMMARY OF INVENTION

Technical Problem

The present invention was achieved in light of the aforementioned circumstances, and it is an object thereof to provide a compound that allows a water-soluble polymer substance such as a nucleic acid or a protein or a medicine to be introduced into a cell or a mucous membrane with a high efficiency using a simple method, and that has a low cytotoxicity and a low mucous membrane irritating property.

Solution to Problem

The inventors of the present invention found that a polysaccharide derivative having a membrane-permeable peptide group in a side chain had a low cytotoxicity and a low mucous membrane irritating property and that such a compound could be used to easily introduce a water-soluble polymer substance such as a nucleic acid or a protein or a medicine into a cell or a mucous membrane, and the present invention was thus achieved.

A polysaccharide derivative having a partial structure represented by Formula (1) below:

[Chem. 1]

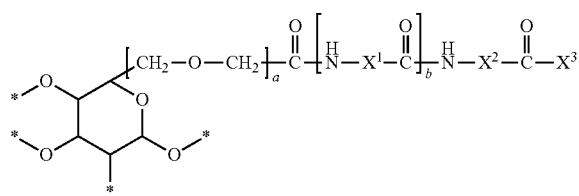

(wherein $X^1$ represents a residue obtained by removing a terminal amino group and a terminal carboxyl group from a neutral amino acid or an ω-aminoalkanoic acid, $X^2$ represents a residue obtained by removing a terminal amino group and a terminal carboxyl group from a membrane-permeable peptide, $X^3$ represents a hydroxyl group, an amino group, an alkoxyl group having 1 to 4 carbon atoms, or a benzyloxy group, a represents a number of 0 or 1, and b represents a number of from 0 to 50.)

Advantageous Effects of Invention

With the present invention, a polysaccharide derivative having a partial structure represented by Formula (1) has a low cytotoxicity and a low mucous membrane irritating property, and can be used without undergoing complex pretreatment to introduce a poorly membrane-permeable compound into a cell or a mucous membrane with a high efficiency.

DESCRIPTION OF EMBODIMENTS

Hereinafter, an example of an embodiment of the present invention will be described, but the present invention is not limited to the following embodiment. It should be noted that a "poorly membrane-permeable compound" as used in the present invention means a compound having a low bioavailability, and specifically a compound having an extent of bioavailability of 50% or less. The extent of bioavailability can be calculated according to the following equation.

Extent of bioavailability (%)=100×(amount of orally administered substance that reaches blood)/(amount of intravenously administered substance that reaches blood)

The "amount of substance that reaches blood" as used herein can be determined as an area of a portion surrounded by a blood level and a horizontal axis (time axis) (area under the drug blood level-time curve: AUC).

A polysaccharide derivative having a partial structure represented by Formula (1) (also referred to as "polysaccharide derivative of the present invention" hereinafter) has a membrane-permeable peptide residue, and allows a poorly membrane-permeable compound to be efficiently taken up by a cell. In a mechanism in which a membrane-permeable peptide is taken up by a cell, generally, a membrane-permeable peptide induces macropinocytosis of a cell and is thus taken up, and it is thought that, when poorly membrane-permeable compounds are present around the membrane-permeable peptide, these poorly membrane-permeable compounds are taken up together with the membrane-permeable peptide. With the polysaccharide derivative of the present invention, macropinocytosis is induced at a plurality of positions of a cell by the membrane-permeable peptide residues, but the polysaccharide derivative of the present invention is a macromolecule, and a cell has a difficulty in taking up a single molecule of the polysaccharide derivative of the present invention at a plurality of positions. Therefore, when poorly membrane-permeable compounds are present around the polysaccharide derivative of the present invention, the poorly membrane-permeable compounds are accidentally and continuously taken up by the cell in which macropinocytosis is induced by the polysaccharide derivative of the present invention. Accordingly, it is thought that interaction between the membrane-permeable peptide residue and the poorly membrane-permeable compound is not necessarily required, and the poorly membrane-permeable compound can be introduced into a cell or a mucous membrane only by bringing a mixture of the polysaccharide derivative of the present invention and the poorly membrane-permeable compound into contact with a cell or a mucous membrane. It should be noted that the mechanisms described herein are merely presumptions, and the present invention is not limited thereto.

Partial Structure Represented by Formula (1)

The partial structure represented by Formula (1) will be described. A saccharide unit shown in Formula (1) may be an L-isomer or a D-isomer, and the saccharide unit shown in Formula (1) may be bound to another saccharide unit via an α-glycoside linkage or a fl-glycoside linkage. In Formula (1), a represents a number of 0 or 1. When a is 1, a plurality of membrane-permeable peptide residues are introduced into the same saccharide unit for the sake of a method of manufacturing the polysaccharide derivative of the present invention, and handleability may be reduced due to an increase in viscosity or an efficiency of introducing a poorly membrane-permeable compound may be reduced. Therefore, it is preferable that a is a number of 0.

In Formula (1), $X^2$ represents a residue obtained by removing the terminal amino group and the terminal carboxyl group from a membrane-permeable peptide. Although the membrane-permeable peptide residue of the polysaccharide derivative of the present invention may be selected as appropriate depending on a cell, a mucous membrane, or a poorly membrane-permeable compound to be introduced, it is preferable that at least one of the amino acids that constitute the membrane-permeable peptide residue is a basic amino acid. The basic amino acid may be an L-isomer or a D-isomer, and may be selected as appropriate depending on a cell, a mucous membrane, or a poorly membrane-permeable compound to be introduced.

Examples of the basic amino acid include arginine, ornithine, lysine, hydroxylysine, and histidine. Of these, an amino acid containing a guanidino group is preferable, and arginine is more preferable. The higher the ratio of the basic amino acid in the membrane-permeable peptide residue is, the more the efficiency of introducing a poorly membrane-permeable compound is improved, and therefore, the molar ratio of the basic amino acids with respect to the total amino acids that constitute the membrane-permeable peptide is preferably 50% or more, and more preferably 70% or more. It is preferable that, out of the amino acids that constitute the membrane-permeable peptide residue, amino acids other than the basic amino acids are neutral amino acids. It should be noted that the term "amino acid" as mentioned herein refers to an α-amino acid unless otherwise stated.

The number of amino acids that constitute the membrane-permeable peptide residue is preferably 5 to 30, more preferably 6 to 20, and even more preferably 7 to 15, because the efficiency of introducing a poorly membrane-permeable compound is improved.

Preferred specific examples of the membrane-permeable peptide include hydrophilic basic peptides such as an arginine oligomer obtained by binding 7 to 30 arginines via peptide bonds, a peptide having an amino acid sequence GRKKRRQRRRPPQ (known by the name HIV-1 Tat: Sequence ID No. 1), a peptide having an amino acid sequence TRQARRNRRRRWRERQR (known by the name HIV-1 Rev: Sequence ID No. 2), a peptide having an amino acid sequence RRRRNRTRRNRRRVR (known by the name FHV Coat: Sequence ID No. 3), a peptide having an amino acid sequence TRRQRTRRARRNR (known by the name HTLV-II Rex: Sequence ID No. 4), and a peptide having an amino acid sequence KLTRAQRRAAARKNKRNTR (known by the name CCMV Gag: Sequence ID No. 5); amphiphilic basic peptides such as a peptide having an amino acid sequence RQIKIWFQNRRMKWKK (known by the name Antennapedia: Sequence ID No. 6), a peptide having an amino acid sequence KMTRAQRRAAAR-RNRWTAR (known by the name BMW Gag: Sequence ID No. 7), a peptide having an amino acid sequence RQIKIW-FQNRRMKWKK (known by the name Penetratin: Sequence ID No. 8), a peptide having an amino acid sequence NAKTRRHERRRKLAIER (known by the name P22N: Sequence ID No. 9), and a peptide having an amino acid sequence DAATATRGRSAASRPTERPRAPARSASR-PDDPVD (known by the name VP22: Sequence ID No. 10); and hydrophobic basic peptides such as a peptide having an amino acid sequence GWTLNSAGYLLGKINLKA-LAALAKKIL (known by the name Transportan: Sequence ID No. 11) and a peptide having an amino acid sequence AGYLLGKINLKALAALAKKIL (known by the name TP-10: Sequence ID No. 12). Of these, the hydrophilic basic peptides are preferable, and the arginine oligomer is more preferable, because the efficiency of introducing a poorly membrane-permeable compound is excellent. The number of repeats of arginine in the arginine oligomer is preferably 7 to 20, more preferably 7 to 15, and even more preferably 7 to 10.

$X^1$ represents a residue obtained by removing the terminal amino group and the terminal carboxyl group from a neutral amino acid or an ω-aminoalkanoic acid, and b represents a number of from 0 to 50. The neutral amino acid may be an L-isomer or a D-isomer. Examples of the neutral α-amino acid include alanine, asparagine, cysteine, glutamine, glycine, isoleucine, leucine, methionine, phenylalanine, proline, serine, threonine, tryptophan, tyrosine, valine, and hydroxyproline, and examples of the ω-aminoalkanoic acid include 3-aminopropanoic acid, 4-aminobutanoic acid, 5-aminopentanoic acid, 6-aminohexanoic acid, 7-aminoheptanoic acid, 8-aminooctanoic acid, 9-aminononanoic acid, 10-aminodecanoic acid, and 11-aminoundecanoic acid. The neutral amino acid applied to $X^1$ is preferably glycine, alanine, valine, isoleucine, leucine, serine, threonine, or phenylalanine, more preferably glycine, alanine, or serine, and even more preferably glycine, because the efficiency of introducing a poorly membrane-permeable compound is improved. b is preferably a number of from 1 to 30, more preferably a number of from 1 to 20, and even more preferably a number of from 1 to 10, from the viewpoint of the efficiency of introducing a poorly membrane-permeable compound and the viewpoint of the ease of synthesis. When b is a number of from 2 to 50, $X^1$ may be one of the neutral amino acid residues or a combination of two or more types.

In Formula (1), $X^3$ represents a hydroxyl group, an amino group, an alkoxyl group having 1 to 4 carbon atoms, or a benzyloxy group. $X^3$ is preferably a hydroxyl group, an amino group, a t-butoxy group, or a benzyloxy group, more preferably a hydroxyl group or an amino group, and even more preferably an amino group, from the viewpoint of the efficiency of introducing a poorly membrane-permeable compound.

When the polysaccharide derivative of the present invention has a plurality of partial structures represented by Formula (1), (—$CH_2$—O—$CH_2$-)$_a$, (—NH—$X^1$—CO—)$_b$, $X^2$, and $X^3$ may be respectively the same or different in the partial structures.

It is preferable that the partial structure represented by Formula (1) is a partial structure represented by Formula (2) below from the viewpoint of the efficiency of introducing a poorly membrane-permeable compound.

[Chem. 2]

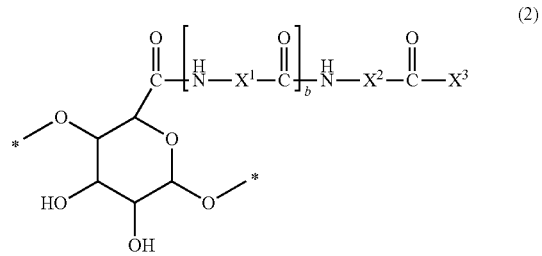

(In the formula, $X^1$ to $X^3$ and b are the same as those defined in Formula (1).)

Polysaccharide Derivative of the Present Invention

The polysaccharide derivative of the present invention will be described. The polysaccharide derivative of the present invention is characterized by having a partial structure represented by Formula (1). When the ratio of the partial structure represented by Formula (1) is too low, the efficiency of introducing a poorly membrane-permeable compound is low, whereas when the ratio of the partial structure represented by Formula (1) is too high, it is difficult to manufacture the polysaccharide derivative of the present invention, and the viscosity of the polysaccharide derivative of the present invention increases, thus reducing the efficiency of introducing a poorly membrane-permeable compound. Therefore, the ratio of the partial structures represented by Formula (1) in the polysaccharide derivative of the present invention with respect to the total saccharide units in the polysaccharide derivative of the present invention is preferably 0.001 to 0.8, more preferably 0.005 to 0.6, and even more preferably 0.01 to 0.5. The ratio as used herein refers to a ratio of the number of partial structures with respect to the number of saccharide units. The saccharide unit as used herein refers to a monosaccharide unit.

When the molecular weight of the polysaccharide derivative of the present invention is too small, the polysaccharide derivative of the present invention itself may be taken up by a cell, and when the molecular weight thereof is too large, the viscosity of polysaccharide derivative of the present invention increases, thus reducing the efficiency of introducing a poorly membrane-permeable compound. Therefore, in terms of a weight-average molecular weight, the molecular weight of the polysaccharide derivative of the present invention is preferably 5,000 to 50,000,000, more preferably 10,000 to 40,000,000, and even more preferably 50,000 to 30,000,000. It should be noted that the "weight-average molecular weight of the polysaccharide derivative of the present invention" as used in the present invention refers to a weight-average molecular weight in terms of pullulan obtained through GPC analysis using an aqueous solvent (the same applies to a polysaccharide derivative having a partial structure represented by Formula (1a), which will be described later).

The polysaccharide derivatives of the present invention is preferably a polysaccharide derivative represented by any of Formulae (3) to (5), and more preferably a polysaccharide derivative represented by Formula (3) because the efficiency of introducing a poorly membrane-permeable compound is high.

[Chem. 3]

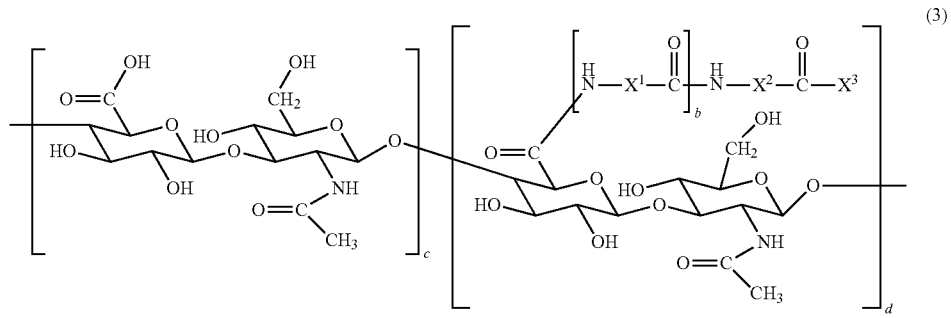

(In the formula, c and d represent numbers satisfying the conditions that c+d is such that the polysaccharide derivative represented by Formula (3) has a weight-average molecular weight of 5,000 to 50,000,000 and d/(c+d) is 0.002 to 1, and $X^1$ to $X^3$ and b are the same as those defined in Formula (1). It should be noted that the c units and the d units are bound to one another in a random manner.)

(In the formula, h, j, k, and m represent numbers satisfying the conditions that h+j+k+m is such that the polysaccharide derivative represented by Formula (5) has a weight-average molecular weight of 5,000 to 50,000,000 and (k+m)/(h+j+k+m) is 0.001 to 1, and $X^1$ to $X^3$ and b are the same as those defined in Formula (1). It should be noted that the h units, the j units, the k units, and the m units are bound to one another in a random manner.)

[Chem. 4]

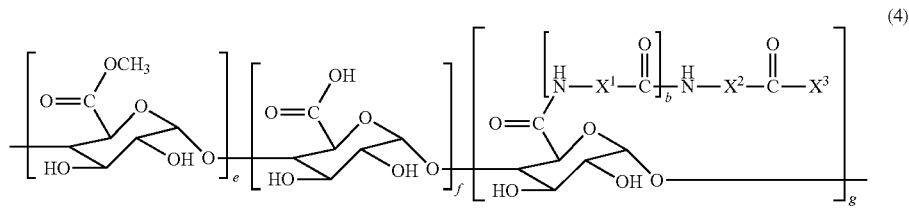

(In the formula, e, f, and g represent numbers satisfying the conditions that e+f+g is such that the polysaccharide derivative represented by Formula (4) has a weight-average molecular weight of 5,000 to 50,000,000 and g/(e+f+g) is 0.001 to 1, and $X^1$ to $X^3$ and b are the same as those defined in Formula (1). It should be noted that the e units, the f units, and the g units are bound to one another in a random manner.)

Method for Manufacturing Polysaccharide Derivative of the Present Invention

The polysaccharide derivative of the present invention can be obtained through a peptide reaction between the carboxyl group of a polysaccharide derivative having a partial structure represented by Formula (1a) below and the amino group of a peptide compound represented by Formula (1b) below. It is sufficient that the reaction between the carboxyl group and the amino group is performed using a

[Chem. 5]

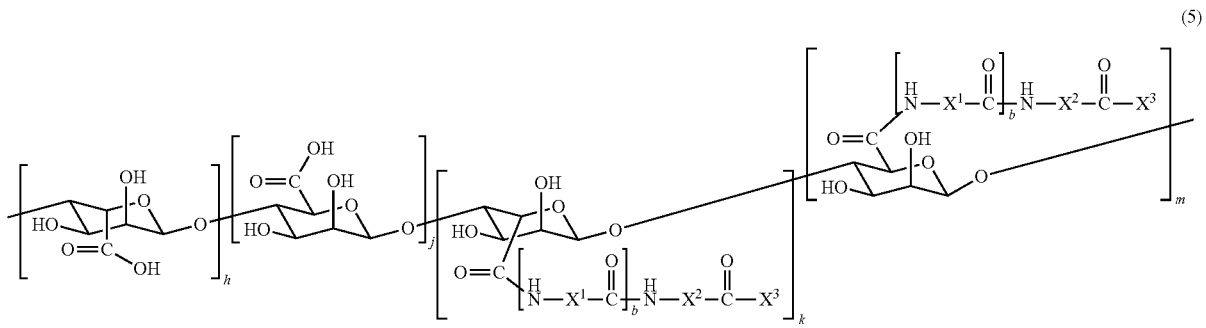

known method, and an example thereof is a method in which a carboxyl group is made into a succinimide ester using N-hydroxysuccinimide, followed by the reaction with an amino group.

[Chem. 6]

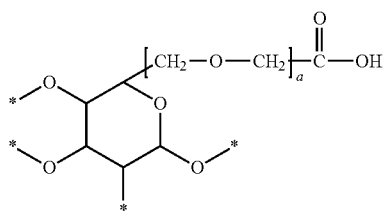

(1a)

(In the formula, a is the same as that defined in Formula (1).)

[Chem. 7]

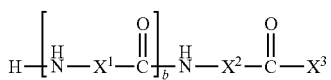

(1b)

(In the formula, $X^1$ to $X^3$ and b are the same as those defined in Formula (1).)

Regarding the polysaccharide derivative having a partial structure represented by Formula (1a), examples of compounds in the derivative, obtained when a is 0 include pectin or pectic acid, hyaluronic acid, and alginic acid; and examples of compounds in the derivative, obtained when a is 1 include carboxymethylated polysaccharide derivatives such as carboxymethylated starch, carboxymethylated cellulose, and carboxymethylated ft glucose. It should be noted that hyaluronic acid is used to obtain the polysaccharide derivative represented by Formula (3), pectin or pectic acid is used to obtain the polysaccharide derivative represented by Formula (4), and alginic acid is used to obtain the polysaccharide derivative represented by Formula (5).

Poorly Membrane-Permeable Compound

The polysaccharide derivative of the present invention can be used as an introducing agent for introducing a poorly membrane-permeable compound into a cell or a mucous membrane to introduce various poorly membrane-permeable compounds. Examples of the poorly membrane-permeable compounds include: drugs such as a peptide/protein drug including insulin, an insulin secretion promoter (e.g., exendin-4 and GLP-1), or the like, a steroid hormone, a non-steroidal analgesic anti-inflammatory drug, a tranquilizer, an anti-hypertensive drug, a therapeutic drug for an ischemic heart disease, an anti-histamine drug, an anti-asthmatic drug, an anti-parkinson drug, a cerebral circulation improving drug, an anti-emetic drug, an anti-depressant drug, an anti-arrhythmic drug, an anti-coagulant drug, an anti-gout drug, an anti-fungal drug, an anti-dementia drug, a therapeutic drug for Sjögren's syndrome, a narcotic analgesic drug, a beta blocker, a β1 agonist, a β2 agonist, a parasympathomimetic drug, an anti-tumor drug, a diuretic drug, an anti-thrombotic drug, a histamine H1 receptor antagonist, a histamine H2 receptor antagonist, an anti-allergic drug, a smoking cessation drug, and a vitamin; nucleic acid compounds such as a deoxyribonucleic acid (DNA), a ribonucleic acid (RNA), and analogs or derivatives thereof (e.g., a peptide nucleic acid (PNA) and a phosphorothioate DNA); peptide compounds such as an enzyme, an antibody, a glycoprotein, and a transcription factor; and polysaccharide derivatives such as pullulan, amylopectin, amylose, glycogen, cyclodextrin, dextran, hydroxyethyldextran, mannan, cellulose, starch, alginic acid, chitin, chitosan, and hyaluronic acid, and derivatives thereof.

Although any of animal cells, plant cells, bacteria, and the like may be used as cells to which the polysaccharide derivative of the present invention is applied, it is preferable to use cells of mammals such as the human from the viewpoint of the efficiency of introducing a poorly membrane-permeable compound. It is also preferable to use cells of mammals such as the human as a mucous membrane to which the polysaccharide derivative of the present invention is applied from the viewpoint of the efficiency of introducing a poorly membrane-permeable compound.

Cell

The polysaccharide derivative of the present invention can be used to introduce a poorly membrane-permeable compound into various types of cells, and thus the poorly membrane-permeable compound can be introduced into any of cells such as cells that are dispersed in a culture solution (also referred to as "liquid culture medium") or the like, cells that adhere to a solid culture medium or the like, and cells of a body tissue. Cells can be broadly divided into adherent cells that include tissue cells, nerve cells, and the like, and floating cells such as hemocytes. A microinjection method or an electroporation method cannot be applied to floating cells, and a calcium phosphate method, a lipofection method, a viral vector method, or the like can be applied thereto, but the introduction efficiency is not satisfying. With the introduction method of the present invention, the poorly membrane-permeable compound can be introduced into not only adherent cells but also floating cells with a high introduction efficiency.

Method of Introduction into Cell

When the polysaccharide derivative of the present invention is used to introduce the poorly membrane-permeable compound into a cell, it is sufficient that an aqueous solution or an aqueous dispersion containing the polysaccharide derivative of the present invention and the poorly membrane-permeable compound is brought into contact with the cell. Therefore, such complex pretreatment that is required in a viral vector method or in a conventional introduction method using a membrane-permeable peptide is not required, and the poorly membrane-permeable compound can be introduced into the cell without a great adverse influence on the cell.

Although examples of an aqueous medium in which the polysaccharide derivative of the present invention and the poorly membrane-permeable compound are dissolved or dispersed to form an aqueous solution or an aqueous dispersion containing these compounds include distilled water and a culture solution to be generally used for cell culture as well as isotonic water such as a physiological saline solution and a 5 mass % aqueous solution of glucose, the culture solution, the physiological saline solution, and the 5 mass % aqueous solution of glucose have little influence on cells and are thus preferable.

When cells are suspended in an aqueous solution or an aqueous dispersion, it is sufficient that the cells are suspended in the aqueous solution or the aqueous dispersion containing the poorly membrane-permeable compound and the polysaccharide derivative of the present invention, and the suspension containing the cells, the poorly membrane-permeable compound, and the polymer compound may be stirred or shaken as needed. When cells cannot be suspended in an aqueous solution or an aqueous dispersion for the reason that the cells adhere to a solid culture medium or a cellular tissue has a large size, it is sufficient that the cells are immersed in the aqueous solution or the aqueous dispersion containing the poorly membrane-permeable compound and the polysaccharide derivative of the present invention.

When the poorly membrane-permeable compound is introduced into a cell, there is no particular limitation on the use concentration of the polysaccharide derivative of the present invention, but it is preferable to set the use concentration to 0.1 μg/mL to 10 mg/mL in the aqueous solution or the aqueous dispersion. Also, there is no particular limitation on the concentration of the poorly membrane-permeable compound to be introduced, but it is preferable to set the concentration to 0.5 μg/mL to 10 mg/mL in the aqueous solution or the aqueous dispersion. Furthermore, there is no limitation on the concentration of cells when the cells are suspended in the aqueous solution or the aqueous dispersion using a culture solution, a physiological saline solution, or the like as a medium, but it is preferable to set the concentration to 10,000 to 2,000,000 cells/mL in the aqueous solution or the aqueous dispersion.

Although there is no limitation on a period of time when the polysaccharide derivative of the present invention, the poorly membrane-permeable compound to be introduced, and the cells are allowed to coexist, it is preferable to set the period of time to 30 minutes to 24 hours.

Mucous Membrane

The polysaccharide derivative of the present invention can be used in a mucous membrane to introduce the poorly membrane-permeable compound into various types of mucous membranes. Examples of the mucous membrane include the nasal mucous membrane, the oral mucous membrane, the vaginal mucous membrane, the rectal mucous membrane, the ocular mucous membrane, the gastric mucous membrane, and the intestinal mucous membrane. A conventional polymer compound having a membrane-permeable peptide in a side chain has a high mucous membrane irritating property and thus causes an itch in some cases when used in the nasal mucous membrane, for example, but with the polysaccharide derivative of the present invention, such an itch is reduced.

Method of Introduction into Mucous Membrane

When the polysaccharide derivative of the present invention is used to introduce the poorly membrane-permeable compound into a mucous membrane, it is sufficient that a mixture of the polysaccharide derivative of the present invention and the poorly membrane-permeable compound is brought into close contact with the mucous membrane, and there is no limitation on a dosage form as long as the mixture has a dosage form that makes it less likely that the mixture separates from the mucous membrane. Although a preferred dosage form varies depending on the type of mucous membrane, examples thereof include a pill, a tablet, a troche, a patch, a suppository, and a poultice. It is sufficient that the form of the mixture of the polysaccharide derivative of the present invention and the poorly membrane-permeable compound is selected from forms such as a liquid form, an emulsion form, a suspension form, a gel form, a powder form, and a solid form depending on the dosage form. One type of the poorly membrane-permeable compounds may be introduced or a combination of two or more types of the poorly membrane-permeable compounds may be introduced according to the purpose. Also, a vehicle, an emulsifier, a dispersant, a gelling agent, a humectant, or the like may be used in addition as needed.

Use of Microprojection Array

The polysaccharide derivative of the present invention cannot be used to introduce the poorly membrane-permeable compound into a cell through the skin, but a microprojection array (a medicine delivery member obtained by arranging minute projections on a sheet; see US 2005025778A1, JP 2008-006178A, and the like, for example) can be used to introduce the poorly membrane-permeable compound into a cell under the skin. For example, the poorly membrane-permeable compound can be introduced into a cell under the skin by attaching, on the skin surface, a microprojection array in which the mixture of the polysaccharide derivative of the present invention and the poorly membrane-permeable compound is applied to the surface or a microprojection array having microprojections including the mixture of the polysaccharide derivative of the present invention and the poorly membrane-permeable compound, passing the minute projections through the skin, and infiltrating the polysaccharide derivative of the present invention and the poorly membrane-permeable compound under the skin.

EXAMPLES

Hereinafter, the present invention will be further described by way of examples, but the present invention is not limited to these examples. It should be noted that, unless otherwise stated, "part" and "%" as used in the examples refer to "part by mass" and "mass %", respectively.

Manufacturing Example 1: Polysaccharide Derivative 1

50 mg of hyaluronic acid (weight-average molecular weight: 5,000 to 150,000) was dissolved in 1 mL of dimethylsulfoxide (DMSO). 47 mg of N-hydroxysuccinimide dissolved in 0.5 mL of DMSO was added to this solution, and then 82 mg of dicyclohexylcarbodiimide (DCC) dissolved in 0.5 mL of DMSO was further added. The resulting solution was stirred at room temperature (25° C.) for 24 hours and reacted. A solid precipitate was filtered out by filtration, and 0.5 mL of DMSO was added to obtain 2.5 mL of a solution of a succinimide ester of hyaluronic acid in DMSO.

0.4 mL of a solution (500 mg/mL) of a compound (manufactured by GL Biochem; product name: RRRRRRRR-NH2, [R=D-Arg] TFA Salt) obtained by amidating the terminal carboxyl group of octaarginine in DMSO was mixed into 1 mL of a solution of the succinimide ester of hyaluronic acid in DMSO, and the resulting solution was stirred at 60° C. for 24 hours and reacted. After the reaction, the reaction solution was poured in a cellulose dialysis tube (seamless cellulose tube; manufactured by Wako Pure Chemical Industries, Ltd.), and the solution in the tube whose both ends were tied up was dialyzed using ion-exchanged water for 2 days. Thereafter, the content of the tube was lyophilized, and thus 102 mg of a polysaccharide derivative 1 of the present invention was obtained. The polysaccharide derivative 1 was a compound represented by Formula (3) in which b was 0, $X^2$ was a residue obtained by removing the terminal amino group and the terminal carboxyl group from octaarginine, $X^3$ was an amino group, and d/(c+d) was 0.58. It should be noted that the value of d/(c+d) was determined using the integral values obtained by NMR. The ratio of the partial structures represented by Formula (1)

with respect to the total saccharide units according to the polysaccharide derivative 1 was calculated as 0.29 using this value of d/(c+d). The polysaccharide derivative 1 had a weight-average molecular weight of 220,000.

Manufacturing Example 2: Polysaccharide Derivative 2

60 mg of a polysaccharide derivative 2 of the present invention was obtained by conducting the operations in the same manner as in Manufacturing Example 1, except that 0.5 mL of a solution (320 mg/mL) of a compound (manufactured by RS Synthesis; product name: H-(Gly)$_4$-(D-Arg)$_8$-NH$_2$ (Purity: 90%), TFA Salt) represented by Formula (1b) in which b was 4, $X^1$ was a residue obtained by removing the terminal amino group and the terminal carboxyl group from glycine, $X^2$ was an octaarginine residue, and $X^3$ was an amino group in DMSO was used instead of 0.4 mL of the solution (500 mg/mL) of the compound obtained by amidating the terminal carboxyl group of octaarginine in DMSO in Manufacturing Example 1. The polysaccharide derivative 2 was a compound represented by Formula (3) in which b was 4, $X^1$ was a residue obtained by removing the terminal amino group and the terminal carboxyl group from glycine, $X^2$ was a residue obtained by removing the terminal amino group and the terminal carboxyl group from octaarginine, $X^3$ was an amino group, and d/(c+d) was 1.0. It should be noted that the value of d/(c+d) was determined using the integral values obtained by NMR. The ratio of the partial structures represented by Formula (1) with respect to the total saccharide units according to the polysaccharide derivative 2 was calculated as 0.5 using this value of d/(c+d). The polysaccharide derivative 2 had a weight-average molecular weight of 370,000.

Comparative Compound 1

A comparative compound 1 was obtained by manufacturing a compound in accordance with Manufacturing Example 1 in JP 2011-229495A. The comparative compound 1 was a compound having the following structure. (In the formula, R represents an arginine residue.)

[Chem. 8]

$$-[CH_2CH]_{70}-[CH_2CH]_{17}-[CH_2CH]_{13}-$$
$$\quad\quad |\quad\quad\quad\quad |\quad\quad\quad\quad |$$
$$\quad\quad NH\quad\quad C=O\quad\quad C=O\quad\quad O$$
$$\quad\quad |\quad\quad\quad\quad |\quad\quad\quad\quad |\quad\quad\quad ||$$
$$\quad\quad C=O\quad\quad OH\quad\quad N-(R)_8-C-NH_2$$
$$\quad\quad |\quad\quad\quad\quad\quad\quad\quad\quad H$$
$$\quad\quad CH_3$$

Comparative Compound 2

A comparative compound 2 was manufactured using chitosan having a weight-average molecular weight of about 100,000 in accordance with the manufacturing example in US 2010113559A1. The comparative compound 2 was a compound having the following structure. (In the formula, R represents an arginine residue, and x:y=80:20.)

[Chem. 9]

(structure showing chitosan derivative with NH$_2$ and NH-C(=O)-(R)$_8$-NH$_2$ groups, repeating units x and y)

Cell

CHO cells: cells derived from the ovaries of Chinese hamsters

Culture Medium

Ham's F12 culture medium (product name; manufactured by Wako)

Opti-MEM culture medium (product name; manufactured by Life Technologies)

Agent

Trypsin-EDTA solution: aqueous solution of 0.25% trypsin and 1 mmol/L EDTA

Cytotoxicity Testing Kit

Cell Counting Kit-8 (product name; manufactured by Dojindo Laboratories)

Poorly Membrane-Permeable Compound

FITC-BSA: Fluorescein-labeled bovine serum albumin (manufactured by Sigma-Aldrich)

Efficiency of Introduction into Cell

500 μL of a suspension (2×10$^5$ cells/mL) of CHO cells in a Ham's F12 culture medium was seeded in each well of a 24-well plate, and preculture was performed in a carbon dioxide incubator for 24 hours. After the supernatant culture medium was removed, 250 μL of a solution (10 μg/mL) of FITC-BSA in an Opti-MEM culture medium was added. Furthermore, 250 μL of a solution (100 μg/mL) of each of the polysaccharide derivatives 1 and 2, and the comparative compounds 1 and 2 in an Opti-MEM culture medium was added, and the cells were cultured in a carbon dioxide incubator for 1 hour. The supernatant culture medium solution was removed, and the cells were washed twice using 500 μL of a phosphate-buffered physiological saline solution. Thereafter, 100 μL of a trypsin-EDTA solution was added, and thus the cultured CHO cells were separated from the plate and dispersed. Next, 100 μL of a 0.08% solution of trypan blue was added, and the cells were suspended and then collected in a microtube. The collected cell suspension was passed through a cell strainer, and MFI (mean fluorescence intensity) was measured using flow cytometry. A sample in which no polysaccharide derivative was used was taken as a blank. Table 1 shows the results.

TABLE 1

|  | MFI |
|---|---|
| Polysaccharide derivative 1 | 122 |
| Polysaccharide derivative 2 | 135 |
| Comparative compound 1 | 127 |
| Comparative compound 2 | 42.4 |
| Blank | 5.64 |

Extracellular FITC-BSA is deactivated by trypan blue and thus emits no fluorescence, and only FITC-BSA that has introduced into a cell emits fluorescence. MFI refers to a mean value of fluorescence intensity per cell, and therefore, a larger MFI value means that FITC-BSA, which is a water-soluble polymer compound as well as a poorly membrane-permeable compound, is taken up by a cell in a larger amount. It is found from the results shown in Table 1 that, when the polysaccharide derivatives 1 and 2 were used, the water-soluble polymer substance was introduced into a cell with a high efficiency.

Cytotoxicity Test

100 μL of a suspension (2×10$^5$ cells/mL) of CHO cells in a Ham's F12 culture medium was seeded in each well of a 96-well plate, and preculture was performed in a carbon dioxide incubator for 24 hours. 10 μL of a solution (2 g/mL) of each of the polysaccharide derivatives 1 and 2, and the comparative compounds 1 and 2 in an Opti-MEM culture medium was added, and the cells were cultured in a carbon dioxide incubator for 1 hour. Furthermore, 10 μL of Cell Counting Kit-8 was added, and the cells were allowed to stand in a carbon dioxide incubator for 1 hour. Thereafter, the absorbance at 450 nm was measured, and the ratio (%) of the absorbance in the presence of each of the polysaccharide derivatives 1 and 2, and the comparative compounds 1 and 2 with respect to the absorbance in the absence of the polysaccharide derivatives 1 and 2, and the comparative compounds 1 and 2 was taken as a cell viability. Table 2 shows the results. It should be noted that a lower cell viability means a higher cytotoxicity.

TABLE 2

|  | Cell viability (%) |
|---|---|
| Polysaccharide derivative 1 | 75 |
| Polysaccharide derivative 2 | 78 |
| Comparative compound 1 | 41 |
| Comparative compound 2 | 62 |

It is found from the results shown in Table 2 that the cell viability was higher in the cases of the polysaccharide derivatives 1 and 2 than in the cases of the comparative compounds 1 and 2, and thus the polysaccharide derivatives 1 and 2 had a lower cytotoxicity.

The invention claimed is:

1. A polysaccharide derivative having a structure represented by one of Formulae (3) to (5) below:

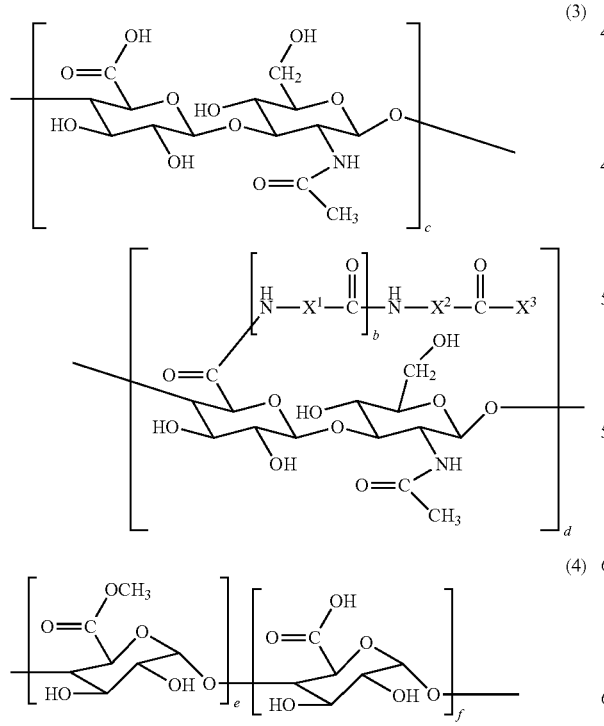

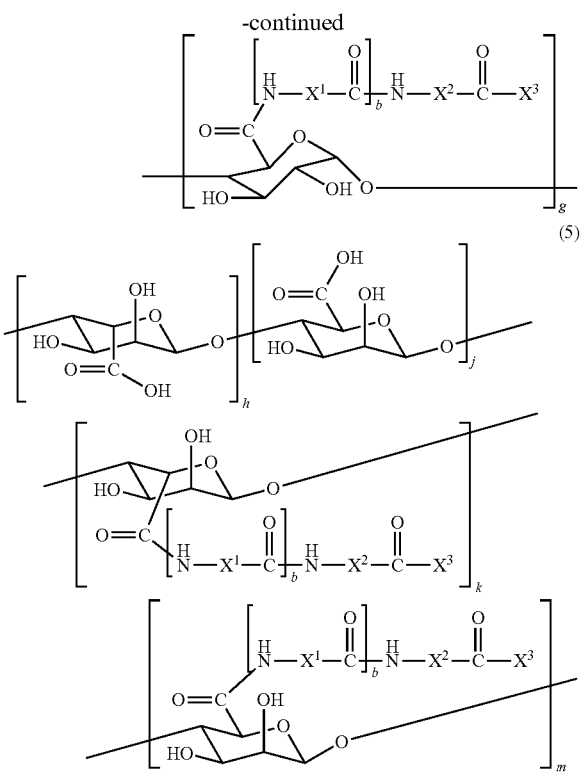

wherein $X^1$ represents a residue obtained by removing a terminal amino group and a terminal carboxyl group from a neutral amino acid or an ω-aminoalkanoic acid, $X^2$ represents a residue obtained by removing a terminal amino group and a terminal carboxyl group from a membrane-permeable peptide, $X^3$ represents a hydroxyl group, an amino group, an alkoxyl group having 1 to 4 carbon atoms, or a benzyloxy group, and b represents a number of from 0 to 50;

c and d represent numbers satisfying the condition that c+d is such that the polysaccharide derivative represented by Formula (3) has a weight-average molecular weight of 5,000 to 50,000,000 and d/(c+d) is such that a ratio of the partial structures represented by Formula (2) below to the total saccharide units in said polysaccharide derivative is from 0.29 to 0.8;

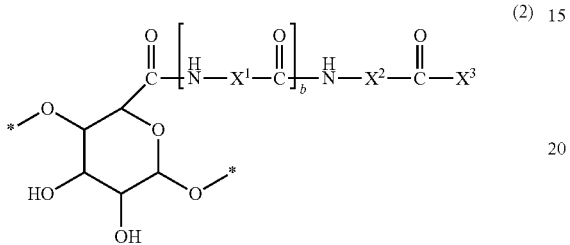

(2)

wherein $X^1$ to $X^3$ and b are as defined in Formulae (3) to (5) and * represents a bonding hand;

e, f and g represent numbers satisfying the condition that e+f+g is such that the polysaccharide derivative represented by Formula (4) has a weight-average molecular weight of 5,000 to 50,000,000 and g/(e+f+g) is such that a ratio of the partial structures represented by Formula (2) to the total saccharide units in said polysaccharide derivative is from 0.29 to 0.8; and h, j, k and m represent numbers satisfying the condition that h+j+k+m is such that the polysaccharide derivative represented by Formula (5) has a weight-average molecular weight of 5,000 to 50,000,000 and (k+m)/(h+j+k+m) is such that a ratio of the partial structures represented by Formula (2) to the total saccharide units in said polysaccharide derivative is from 0.29 to 0.8.

2. The polysaccharide derivative according to claim 1, wherein at least one of the amino acids that constitute $X^2$ in Formula (1) is a basic amino acid.

3. The polysaccharide derivative according to claim 1, wherein the polysaccharide derivative is a polysaccharide derivative represented by Formula (3), provided that the c units and the d units are bound to one another in a random manner.

4. An introducing agent for introducing a poorly membrane-permeable compound into a cell or a mucous membrane, the introducing agent comprising the polysaccharide derivative according to claim 1.

5. A method for introducing a poorly membrane-permeable compound into a cell, the method comprising:
contacting the cell with an aqueous solution containing the introducing agent according to claim 4 and the poorly membrane-permeable compound or an aqueous dispersion containing the introducing agent and the poorly membrane-permeable compound, or
attaching, on a skin surface, a microprojection array in which the mixture containing the introducing agent according to claim 4 and the poorly membrane-permeable compound is applied to the surface or a microprojection array having microprojections including the mixture containing the introducing agent and the poorly membrane-permeable compound, passing minute projections of the microprojection array through the skin, and infiltrating the introducing agent and the poorly membrane-permeable compound under the skin.

6. A method for introducing a poorly membrane-permeable compound into a mucous membrane, the method comprising contacting the mucous membrane with a mixture containing the introducing agent according to claim 4 and the poorly membrane-permeable compound.

7. An introducing agent for introducing a poorly membrane-permeable compound into a cell or a mucous membrane, the introducing agent comprising the polysaccharide derivative according to claim 2.

8. The method according to claim 5,
wherein the poorly membrane-permeable compound is a protein drug, an enzyme, an antibody or a glycoprotein.

9. The method according to claim 6,
wherein the poorly membrane-permeable compound is a protein drug, an enzyme, an antibody or a glycoprotein.

10. The polysaccharide derivative according to claim 1, wherein b represents a number of from 2 to 50; and
wherein $X^1$ is the residue of a neutral amino acid selected from the group consisting of asparagine, glutamine, glycine, methionine, phenylalanine, proline, threonine and hydroxyproline.

11. The polysaccharide derivative according to claim 1, wherein b represents a number of from 2 to 50; and
wherein $X^1$ is the residue of a neutral amino acid selected from the group consisting of alanine, asparagine, cysteine, glutamine, glycine, isoleucine, leucine, methionine, phenylalanine, proline, serine, threonine, tryptophan, valine and hydroxyproline.

\* \* \* \* \*